(12) United States Patent
Shkolnik

(10) Patent No.: US 6,322,534 B1
(45) Date of Patent: Nov. 27, 2001

(54) VARIABLE STIFFNESS BALLOON CATHETER

(75) Inventor: Boris Shkolnik, Aventura, FL (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 09/415,532

(22) Filed: Oct. 8, 1999

Related U.S. Application Data

(60) Provisional application No. 60/107,521, filed on Nov. 7, 1998.

(51) Int. Cl.$^7$ ................................................. A61M 29/00
(52) U.S. Cl. ............................................. 604/96.01
(58) Field of Search .................... 604/96.01, 97, 604/99, 103, 104, 264; 606/191–194

(56) References Cited

U.S. PATENT DOCUMENTS

| | | |
|---|---|---|
| 3,416,531 | 12/1968 | Edwards . |
| 3,640,282 | 2/1972 | Kamen et al. . |
| 3,924,632 | 12/1975 | Cook . |
| 4,020,829 | 5/1977 | Wilson et al. . |
| 4,425,919 | 1/1984 | Alston, Jr. et al. . |
| 4,516,972 | 5/1985 | Samson . |
| 4,545,390 | 10/1985 | Leary . |
| 4,579,127 | 4/1986 | Haacke . |
| 4,586,923 | 5/1986 | Gould et al. . |
| 4,739,768 | 4/1988 | Engelson . |
| 4,764,324 | 8/1988 | Burnham . |
| 4,798,598 | 1/1989 | Bonello et al. . |
| 4,811,737 | 3/1989 | Rydell . |
| 4,817,613 | 4/1989 | Jaraczewski et al. . |
| 4,899,787 | 2/1990 | Ouchi et al. . |
| 4,921,478 | 5/1990 | Solano et al. . |
| 4,921,483 | 5/1990 | Wijay et al. . |
| 4,976,690 | * 12/1990 | Solar et al. . |
| 4,981,478 | * 1/1991 | Evard et al. . |
| 5,035,705 | * 7/1991 | Burns . |
| 5,037,404 | 8/1991 | Gold et al. . |
| 5,045,072 | * 9/1991 | Castillo et al. . |
| 5,057,092 | * 10/1991 | Webster, Jr. . |
| 5,061,257 | * 10/1991 | Martinez et al. . |
| 5,069,217 | 12/1991 | Fleischhacker, Jr. . |
| 5,131,407 | 7/1992 | Ischinger et al. . |
| 5,135,486 | * 8/1992 | Eberle et al. . |
| 5,147,317 | 9/1992 | Shank et al. . |
| 5,176,661 | * 1/1993 | Evard et al. . |
| 5,176,698 | * 1/1993 | Burns et al. . |
| 5,209,735 | 5/1993 | Lazarus . |
| 5,251,640 | 10/1993 | Osborne . |
| 5,256,145 | * 10/1993 | Atkinson et al. . |
| 5,437,632 | 8/1995 | Engelson . |
| 5,460,187 | 10/1995 | Daigle et al. . |
| 5,460,608 | 10/1995 | Lodin et al. . |

(List continued on next page.)

FOREIGN PATENT DOCUMENTS

| | | |
|---|---|---|
| 0 358 117 | 5/1995 | (EP) . |
| 0 555 088 B1 | 1/1998 | (EP) . |
| 0 823 262 | 2/1998 | (EP) . |
| WO 91/17782 | 11/1991 | (WO) . |
| WO 93/02733 | 2/1993 | (WO) . |

*Primary Examiner*—Manuel Mendez
(74) *Attorney, Agent, or Firm*—Henry W. Collins

(57) ABSTRACT

An improved balloon catheter which may be used for angioplasty or for placing a reinforcing stent into a human vessel which has a variable stiffness catheter portion for guiding the catheter through the vasculature. The catheter portion of the balloon catheter includes a relatively stiff shaft portion which is reinforced with braided layer and more flexible distal portion which is reinforced with a single helically wire coil so that the relatively stiff shaft portion may be advanced along a guidewire and the more flexible distal portion may be guided through the tortuous vasculature.

5 Claims, 1 Drawing Sheet

U.S. PATENT DOCUMENTS

| | | |
|---|---|---|
| 5,470,315 | 11/1995 | Adams . |
| 5,514,073 * | 5/1996 | Miyata et al. . |
| 5,676,659 * | 10/1997 | McGurk . |
| 5,728,063 * | 3/1998 | Preissman et al. . |
| 5,728,065 * | 3/1998 | Follmer et al. . |
| 5,749,849 | 5/1998 | Engelson . |
| 5,759,173 | 6/1998 | Preissman et al. . |
| 5,876,376 | 3/1999 | Schwab et al. . |

* cited by examiner

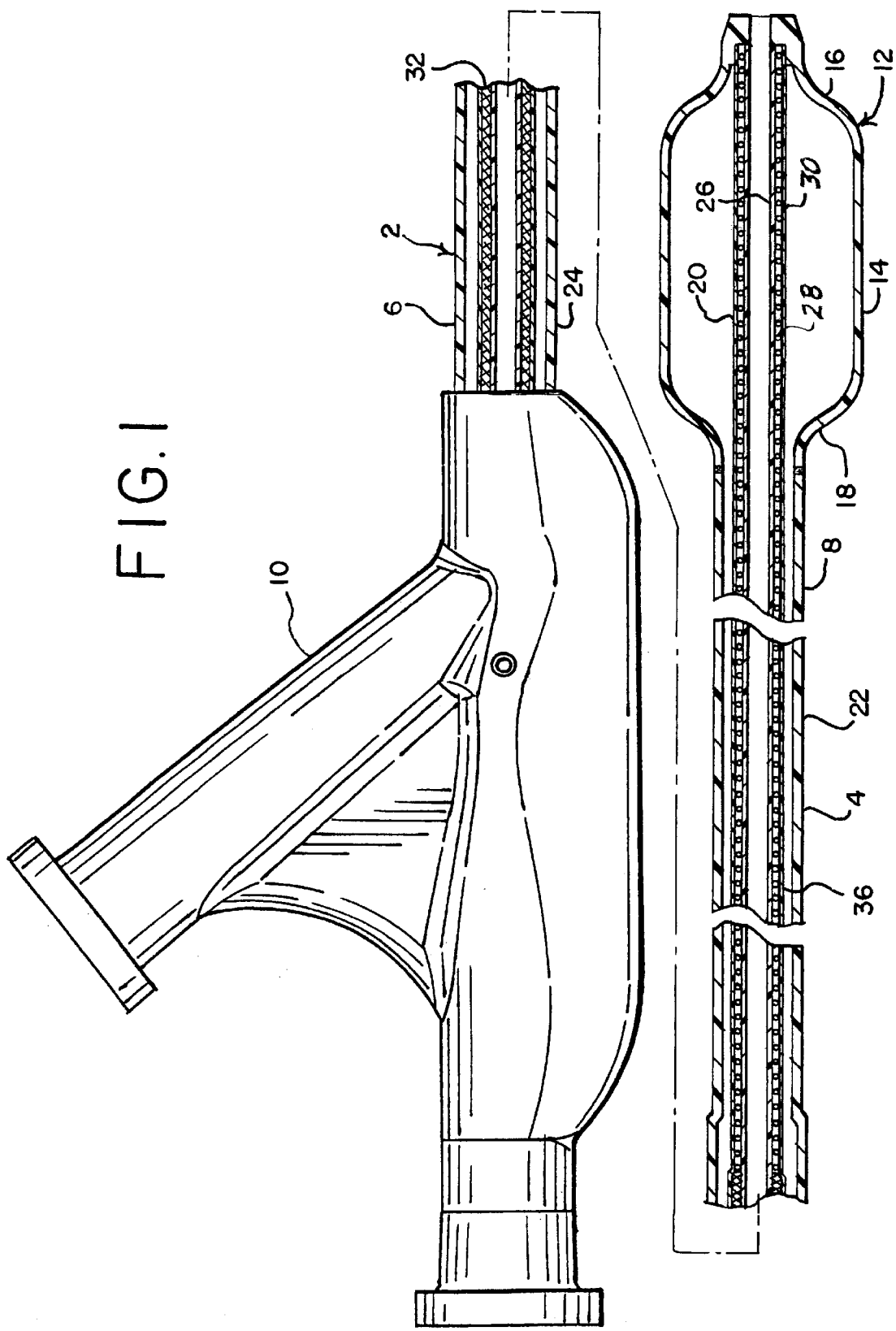

VARIABLE STIFFNESS BALLOON CATHETER

This Appln claims benefit of Provisional No. 60/107,521 filed Nov. 7, 1998.

BACKGROUND OF THE INVENTION

1. Field of the Invention

This invention relates to vascular balloon catheters which may be used for percutaneous transluminal angioplasty procedures, or alternatively may be used to position and expand a reinforcing stent within a blood vessel. In particular, the invention is especially adapted to treatment of small diameter blood vessels within the brain and may, for example, be used to temporarily occlude a blood vessel to evaluate the results of the occlusion prior to placing a permanent occlusion device within the vessel.

2. Description of the Prior Art

Medical catheters exist for a wide variety of purposes, including diagnostic procedures and interventional therapy including drug delivery, drainage, and perfusion. Catheters for each of these purposes may be introduced to numerous target sites within a patient's body by guiding the catheter through the vascular system. A wide variety of specific catheter designs have been proposed for such different uses.

Of particular interest to the present invention, small diameter tubular access catheters are presently being used for diagnostic and interventional therapy techniques for vessels within the brain, such as the imaging and treatment of aneurysms, tumors, arteriovenous malformations and fistulas. Such techniques place a number of requirements on catheters which are to be employed. The primary requirement is size. The blood vessels in the brain are frequently as small as several millimeters, or less, requiring that catheters have an outside diameter as small as one French (0.33 millimeters). In addition to small size, the brain vasculature is highly tortuous, requiring that catheters for use in vessels of the brain be very flexible, particularly at their distal ends, to pass through the regions of tortuosity. Difficulties in catheter positioning, however, make it desirable to impart high tensile and column strength over at least the proximal portion of the catheter. Additionally, the blood vessels of the brain are relatively fragile, so it is desirable that the catheters have a soft, non-traumatic exterior to prevent injury.

It would therefore be desirable to provide improved small diameter, flexible balloon catheters suitable for introduction to very small blood vessels, particularly to the vasculature of the brain. Such balloon catheters should provide sufficient flexibility to permit access to the tortuous regions of this vasculature, while retaining sufficient tensile, column, and hoop strengths to enhance resistance to kinking and collapse. The improved catheters should also have enhanced positioning characteristics, including pushability and torqueability. Additionally, it would be desirable to have an improved wall strength over a portion or all of the catheter wall to resist bursting and failure when introducing high pressure fluids.

U.S. Pat. No. 4,739,768, describes a catheter consisting of an inner layer and an outer layer, where the inner layer terminates proximally of the outer layer to form a relatively more flexible distal end. World Patent No. 91/17782 describes a catheter having a braid-reinforced distal end with a low friction surface. World Patent No. 93/02733 describes a catheter having four regions of different stiffness. Braid and otherwise reinforced catheter structures are described in U.S. Pat. Nos. 3,416,531; 3,924,632; 4,425,919; 4,586,923; 4,764,324; 4,817,613; 4,899,787; 5,045,072; 5,057,092; 5,061,257; and European Patent No. 555088. U.S. Pat. No. 4.921,478 to Solano et al. shows a cerebral balloon catheter having an open central lumen and a specially shaped balloon.

U.S. Pat. No. 4,976,690 describes a variable stiffness angioplastic catheter in which the stiffness of the catheter is generally controlled by utilizing various catheter wall thicknesses and catheter diameters in order to provide a balloon catheter with a relatively stiff proximal portion and a more flexible distal portion.

U.S. Pat. No. 5,728,065 discloses a balloon catheter in which a flat helical coil is embedded along the length of the inner tubular body of the catheter for providing a relatively stiff proximal portion and in which the turns of the helical coil are spaced apart at the distal portion of the catheter in order to provide for a more flexible distal portion.

SUMMARY OF THE INVENTION

In accordance with the present invention, there is provided a balloon catheter which includes an inner catheter body comprised of an inner tubular member, a braided reinforcing layer disposed over the inner tubular member and extending from the proximal end of the inner tubular member and terminating at its distal end at a distance in a range of between about 10 and 70 centimeters from the distal tip of the inner tubular member. A coil reinforcing layer comprised of single metallic wire is formed in a helical configuration and is disposed over the remainder of the inner tubular member, i.e. extending from the distal end of the braided layer to about the distal end of the inner tubular member. An outer layer of a soft polymer material is formed over the braided reinforcing layer and coil reinforcing layer and generally extends from the proximal end to the distal end of the inner tubular member. The balloon catheter also includes an outer tubular member extending coaxially over the inner tubular member to form an inflation lumen between the outer and inner tubular members. The outer tubular member extends from the proximal end of the inner tubular member and terminates short of the distal end of the inner tubular member. An inflatable balloon having proximal and distal portions extending from the body portion of the balloon extends coaxially over the inner tubular member at the distal end of this member and the proximal portion of the balloon is sealed in fluid-tight relationship to the distal end of the outer tubular member. The distal portion of the inflatable balloon is sealed in fluid-tight relationship with the distal end of the inner tubular member. In addition, a coupling member, such as a Y-connector, having a lumen extending therethrough is mounted on the proximal end of the outer tubular member and the lumen of the coupling member is in fluid communication with the lumen between the outer tubular member and the inner tubular member in order that fluid may be injected into the lumen of the coupling to thereby inflate the balloon.

In accordance with another aspect of the present invention, the braided reinforcing layer is comprised of braided wrapped onto the outer surface of the inner tubular member. Preferably, the braided strands are formed of stainless steel wires.

In accordance with still another aspect of the present invention, the coil reinforcing layer is comprised of a single wire of circular cross section which is helically wrapped around the outer surface of the inner tubular member. Preferably, the wire is formed from platinum.

In accordance with still another aspect of the present invention, the outer tubular member has a proximal portion and a distal portion in which the distal portion has an outer diameter less than the outer diameter of the proximal portion of the outer tubular member. Preferably, the distal portion of the outer tubular member also has an inner diameter which is less than the inner diameter of the proximal portion of the outer tubular member.

Accordingly, with this construction of the catheter portion of the balloon catheter, the proximal portion of the catheter body remains relatively stiff so that the catheter may be pushed into and through the vasculature of the human body and the distal portion of the catheter body is constructed in a manner to be very flexible in order to track through the very tortuous vascular of the human body.

BRIEF DESCRIPTION OF THE DRAWING

FIG. 1 is a cross-sectional view illustrating a balloon catheter made in accordance with the invention.

DESCRIPTION OF A PREFERRED EMBODIMENT

FIG. 1 illustrates a simplified cross sectional view of a balloon catheter made in accordance with the present invention. The balloon catheter 2 includes an outer sheath 4 having a proximal end 6 and a distal end 8. A dual port wire connector 10 is coupled to the proximal end 6 of the outer sheath 4. An inflatable balloon 12 having a main body portion 14 and proximal and distal portions 18, 16, respectively, is secured to the distal end of the outer sheath 4 by the proximal balloon portion 18. The distal portion 16 of the inflatable balloon is, in turn, secured to the distal end of an inner tubular member 20. As illustrated, the outer sheath 4 includes a distal portion 22 and a proximal portion 24 of differing diameters. The proximal portion 24 is formed from nylon having a durometer of 75 D, and the distal portion 22 is formed of polyurethane having a durometer of 65 D. In addition, the outside diameter of the proximal portion 24 of the outer sheath is approximately 0.043 inches, the inside diameter of this proximal portion is 0.038 inches with the result that the wall thickness of the proximal portion of the outer sheath is about 0.0025 inches. The distal portion 22 of the outer sheath has an outer diameter of 0.0365 inches, an inside diameter of 0.0315 inches with the result that the wall thickness of the distal portion of the outer sheath is about 0.0025 inches. With the resulting reduction in diameter of the proximal portion of the outer sheath 4, the distal section of the catheter becomes more flexible and therefore may be more easily passed through the tortuous vessels of the human body.

Most importantly, the present invention provides an improved construction of the inner tubular member 20 or inner body. The inner tubular member 20 is comprised of a thin inner layer 26, a reinforcing layer 28 placed on top of the inner layer 26 and a soft outer layer 30 which surrounds and bounds the reinforcing layer 28 to the inner layer 26. The reinforcing layer 28 is comprised of a proximal reinforcing layer 32 which is formed from braided stainless steel wires and a distal reinforcing layer 36 which is formed from a single helically wound platinum wire. The soft outer layer 30 is heat bonded onto the reinforcing layer 28. Accordingly, with the proximal section of the catheter having an inner tubular member formed with a braided reinforcing layer, this section of the catheter becomes relatively stiff and has a relatively high column strength so that the catheter may be pushed into and through the vasculature of the human body. On the other hand, the distal section of the catheter is formed with an inner tubular member which is comprised of a single helically wound wire which, while being sufficiently stiff to resist kinking, is still very flexible and is capable of traversing tortuous vessels.

As may now be appreciated, with the balloon catheter as illustrated in FIG. 1, the proximal section of the catheter is formed with an outer sheath portion of an increased diameter and an inner tubular member which is formed by bonding a reinforcing layer of woven stainless steel wires between two polymer layers thereby providing a proximal catheter section which exhibits the characteristic of having relatively high column strength. The distal section of the catheter is formed with an outer sheath having a reduced diameter, both outer diameter and inner diameter, and also with a single helically wound wire bonded between two polymer tubular members to thereby provide a distal section which is relatively kink resistant, but still remains very flexible.

In a preferred construction of the present invention, the outer sheath 4 is formed from polyurethane material and the inflatable balloon is formed from silicone material. The outside diameter of the proximal section of the outer sheath 4 has an outside diameter of 0.043 inches and an inside diameter of 0.058 inches. The distal section of the outer sheath 4 has an outside diameter of 0.0365 inches and in inside diameter of 0.0315 inches. In addition, the thin inner layer 26 of the inner tube member 20 is formed from PTFE material and has a thickness of approximately 0.0015 inches. The soft outer layer 30 of the inner tubular member 20 is preferably formed of polyurethane material and has a thickness of approximately 0.0025 inches.

The helical wound coil in the distal reinforcing layer 34 is formed of platinum wire having a circular cross section and with a diameter of approximately 0.0015 inches, and the braiding in the proximal reinforcing layer 32 is formed of stainless steel wire of circular cross-section. The wire forming the stainless steel braid preferably has a diameter of about 0.0015 inches.

With the balloon catheter of the present invention, fluid may be applied through a lumen in the side port of the wire connector 10 which communicates with the passageway between the inner tubular member 20 and the outer sheath 4 to thereby inflate the balloon 12. In order to steer the catheter through the vasculature, a guidewire is typically passed through the proximal port of the wire connector 10 and through the inner lumen of the inner tubular member which serves to assist in steering the distal tip of the catheter through the vasculature.

The invention has now been explained with reference to a specific embodiment. Other embodiments will be apparent to those of ordinary skill in the art upon reference to this disclosure. It is therefore not intended that this invention be limited except as indicated by the appended claims.

That which is claimed is:

1. A balloon catheter comprising:
    an inner catheter body having proximal and distal ends and comprising:
        an inner tubular member having proximal and distal ends and a lumen extending therethrough;
        a braided reinforcing layer disposed over the inner tubular member and extending from the proximal end of the inner tubular member and terminating at its distal end at a distance in a range of between about 50 and 70 centimeters from the distal end of the inner tubular member, said braided reinforcing layer formed of circular cross-section wire;
        a coil reinforcing layer comprised of a single metallic wire of a circular cross-section formed in helical configuration disposed over the inner tubular member and extending from the distal end of the braided layer to about the distal end of the inner tubular member;

a thin outer layer formed over the braided reinforcing layer and the coil reinforcing layer and extending from the proximal end to the distal end of the inner tubular member;

an outer tubular member extending coaxially over the inner tubular member to form an inflation lumen between the outer and inner tubular members and having a proximal end and a distal end which terminates proximally from the distal end of the inner tubular member, said outer tubular member including a proximal portion formed of a material having a durometer of about 75 D and a distal portion formed of a material having a durometer of about 65 D;

an inflatable balloon having a main body portion and proximal and distal portions extending from the main body portion, said proximal portion of the balloon sealed to the distal end of the outer tubular member and said distal portion of the balloon being sealed to the distal end of the inner tubular member; and a coupling member having a lumen extending therethrough, said coupling member being mounted on the proximal end of the outer tubular member and the lumen of the coupling member communicating with the lumen between the outer tubular member and the inner tubular member so that fluid may be injected into the lumen of the coupling member to inflate the balloon.

2. A balloon catheter as defined in claim 1, wherein the braided reinforcing layer is comprised of braided stainless steel wires wrapped onto the inner tubular member.

3. A balloon catheter as defined in claim 2, wherein the coil reinforcing layer is comprised of a single platinum wire of circular cross-section which is helically wrapped around the inner tubular member.

4. A balloon catheter as defined in claim 1, wherein the proximal portion of the outer tubular member is comprised of nylon and a distal portion of the outer tubular member is comprised of polyurethane and in which the distal portion of the outer tubular member has an outer diameter less than the outer diameter of the proximal portion of the outer tubular member.

5. A balloon catheter as defined in claim 5, wherein the distal portion of the outer tubular member has an inner diameter less than the inner diameter of the proximal portion of the outer tubular member.

* * * * *